United States Patent [19]

Shinohara et al.

[11] Patent Number: 4,663,471

[45] Date of Patent: May 5, 1987

[54] METHOD FOR THE PREPARATION OF N-METHYL-N-TRIMETHYLSILYL TRIFLUOROACETAMIDE

[75] Inventors: Toshio Shinohara, Takasaki; Yoshifumi Inoue, Annaka, both of Japan

[73] Assignee: Shin-Etsu Chemical Co., Ltd., Tokyo, Japan

[21] Appl. No.: 896,280

[22] Filed: Aug. 14, 1986

[51] Int. Cl.$^4$ ............................................... C07F 7/10
[52] U.S. Cl. .................................................... 556/411
[58] Field of Search ......................................... 556/411

[56] References Cited

U.S. PATENT DOCUMENTS 3,415,864 12/1968 Gehrke et al. ...................... 556/411
3,839,387 10/1974 Chou et al. ......................... 556/411

*Primary Examiner*—Paul F. Shaver
*Attorney, Agent, or Firm*—Hopgood, Calimafde, Kalil, Blaustein & Judlowe

[57] ABSTRACT

N-Methyl-N-trimethylsilyl trifluoroacetamide can be synthesized by the reaction of N-methyl trifluoroacetamide and, N,O-bis(trimethylsilyl) acetamide at 40°–130° C. followed by fractionating distillation. The method is advantageous in respect of the absence of the step of filtration for the removal of the by-product salt and non-use of any corrosive reactant in comparison with conventional methods.

3 Claims, No Drawings

METHOD FOR THE PREPARATION OF N-METHYL-N-TRIMETHYLSILYL TRIFLUOROACETAMIDE

BACKGROUND OF THE INVENTION

The present invention relates to a method for the preparation of N-methyl-N-trimethylsilyl trifluoroacetamide or, more particularly, to an industrially advantageous method for the preparation of N-methyl-N-trimethylsilyl trifluoroacetamide without using corrosive reactants and with omission of the troublesome procedure of filtration to remove the precipitates of a by-product salt.

N-Methyl-N-trimethylsilyl trifluoroacetamide as the subject material of the inventive method is a useful compound as a neutral masking agent, i.e. a masking reactant for active hydrogen atoms utilizing the silyl group, in the semi-synthetic process of various antibiotics or derivatives thereof.

It is known and conventionally practiced in the synthetic preparation of N-methyl-N-trimethylsilyl trifluoroacetamide that N-methyl trifluoroacetamide is subjected to a dehydrochlorination reaction with trimethyl chlorosilane by adding the silane compound dropwise into a reaction mixture of N-methyl trifluoroacetamide and a tertiary amine compound, e.g. triethyl amine, as an acceptor of hydrogen chloride diluted with an organic solvent such as benzene, hexane and the like.

This method, however, is disadvantageous in several respects. For example, the reaction mixture after completion of the dehydrochlorination reaction must be filtered to remove the precipitates of the amine hydrochloride while the filtration cannot be performed without the problem of emission of a large volume of white fume by the reaction of the atmospheric moisture with the tertiary amine compound and trimethyl chlorosilane remaining in the reaction mixture to cause serious environmental pollution if not to mention the decrease in the yield of the product by the filtration and hydrolysis of the product compound during filtration. Moreover, the chlorosilane compound as one of the reactants is very corrosive against metals so that the production cost is necessarily high due to the expensiveness of the corrosion-resistant apparatus used in the preparation.

SUMMARY OF THE INVENTION

Thus, the method of the invention for the preparation of N-methyl-N-trimethylsilyl trifluoroacetamide, developed as a result of the investigations to solve the above described problems and disadvantages in the prior art method, comprises:

(a) mixing N-methyl trifluoroacetamide and N,O-bis(-trimethylsilyl) acetamide to form a reaction mixture; and (b) heating the reaction mixture.

The reaction of the reactants above mentioned, neither of them being corrosive, proceeds so smoothly without producing any precipitates as a by-product that no filtration of the reaction mixture after completion of the reaction is necessary and the desired product can be isolated by merely fractionating the reaction mixture by distillation.

DETAILED DESCRIPTION OF THE PREFERRED EMBODIMENTS

As is described above, the principle of the inventive method is the reaction of N-methyl trifluoroacetamide and N,O-bis(trimethylsilyl) acetamide, which can be prepared according to the disclosure in U.S. Pat. No. 3,397,220, according to the following reaction equation, in which Me denotes a methyl group:

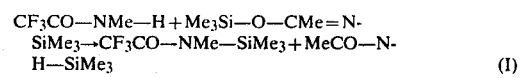

$$CF_3CO-NMe-H + Me_3Si-O-CMe=N-SiMe_3 \rightarrow CF_3CO-NMe-SiMe_3 + MeCO-N-H-SiMe_3 \qquad (I)$$

The velocity of this reaction is low at room temperature so that the reaction mixture should be heated at a temperature in the range from 40° to 130° C. When the temperature is lower than 40° C., the reaction proceeds so slowly that the yield of the desired product cannot be high enough within a reasonable time of reaction while the N,O-bis(trimethylsilyl) acetamide may be subject to thermal decomposition when the reaction mixture is heated at a temperature higher than 130° C. also to decrease the yield of the desired product. The reaction is usually complete within 2 to 4 hours. It is preferable that the amount of N,O-bis(trimethylsilyl) acetamide is somewhat larger than equimolar to N-methyl trifluoroacetamide or the molar ratio of the former reactant to the latter reactant should be in the range from 1:1 to 1.3:1 in consideration of the balance between the yield of the product and the cost for the reactants. The reaction mixture may be diluted with an organic solvent such as hydrocarbons, e.g. benzene and hexane, if necessary, although the reaction can proceed without using any solvent.

When the reaction is completed in the above described manner, the reaction mixture is first freed from the solvent, when used, by distillation and then subjected to fractionating distillation under reduced pressure at a temperature of 130° C. or below to isolate the desired product of N-methyl-N-trimethylsilyl trifluoroacetamide. The yield of the product is usually at least 90% of the theoretical value. N-Trimethylsilyl acetamide produced as a by-product is also useful as a silylating agent.

In the following, examples are given to illustrate the inventive method in more detail.

EXAMPLE 1.

Into a three-necked flask of 2-liter capacity equipped with a stirrer, reflux condenser and thermometer were introduced 254 g (2.00 moles) of N-methyl trifluoroacetamide, 528 g (2.60 moles) of N,O-bis(trimethylsilyl) acetamide and 400 ml of benzene to form a reaction mixture, which was heated at 80° C. under agitation for 3 hours. After cooling, the solvent was removed from the mixture by distillation and the remaining mixture was distilled under reduced pressure to give 364 g of a fraction boiling at 52° to 54° C. under a pressure of 40 mmHg, which was identified to be N-methyl-N-trimethylsilyl trifluoroacetamide. The yield of the product was 91% of the theoretical value.

EXAMPLE 2

Into a three-necked flask of 500-ml capacity equipped with a stirrer, reflux condenser and thermometer were introduced 127 g (1.00 mole) of N-methyl trifluoroacetamide and 244 g (1.20 moles) of N,O-bis(- trimethylsilyl) acetamide to form a reaction mixture, which was heated at 100° C. under agitation for 4 hours. After cooling, the mixture was distilled under reduced pressure to give 188 g of a fraction boiling at 52° to 54° C. under a pressure of 40 mmHg, which was identififed to be N-methyl-N-trimethylsilyl trifluoroacetamide. The yield of the product was 94% of the theoretical value.

What is claimed is:

1. A method for the preparation of N-methyl-N-trimethylsilyl trifluoroacetamide which comprises:

(a) mixing N-methyl trifluoroacetamide and N,O-bis(-trimethylsilyl) acetamide to form a reaction mixture; and
    (b) heating the reaction mixture.

2. The method for the preparation of N-methyl-N-trimethylsilyl trifluoroacetamide as claimed in claim 1 wherein the reaction mixture is heated at a temperature in the range from 40° to 130° C.

3. The method for the preparation of N-methyl-N-trimethylsilyl trifluoroacetamide as claimed in claim 1 wherein N-methyl trifluoroacetamide and N,O-bis(-trimethylsilyl) acetamide are mixed in a molar ratio in the range from 1:1 to 1:1.3.

* * * * *